United States Patent [19]

Miyazaki

[11] Patent Number: 4,926,257
[45] Date of Patent: May 15, 1990

[54] STEREOSCOPIC ELECTRONIC ENDOSCOPE DEVICE

[75] Inventor: Akihiko Miyazaki, Hachioji, Japan

[73] Assignee: Olympus Optical Co., Ltd., Tokyo, Japan

[21] Appl. No.: 135,178

[22] Filed: Dec. 18, 1987

[30] Foreign Application Priority Data

Dec. 19, 1986 [JP] Japan .................. 61-303286

[51] Int. Cl.⁵ .................. H04N 7/18; H04N 13/00; A61B 1/06
[52] U.S. Cl. .................. 358/98; 358/88; 350/516; 128/6
[58] Field of Search .......... 358/3, 88, 98; 128/4, 128/6; 350/516

[56] References Cited

U.S. PATENT DOCUMENTS

| | | | |
|---|---|---|---|
| 3,520,587 | 7/1970 | Tasaki et al. | 358/901 |
| 4,061,135 | 12/1977 | Widran et al. | 128/6 |
| 4,364,629 | 12/1982 | Lang et al. | 350/516 |
| 4,412,127 | 10/1983 | Imai | 350/516 |
| 4,651,201 | 3/1987 | Schoolman | 358/98 |
| 4,734,756 | 3/1988 | Butterfield et al. | 358/88 |
| 4,807,026 | 2/1989 | Nishioka et al. | 358/98 |

FOREIGN PATENT DOCUMENTS

| | | |
|---|---|---|
| 48-25360 | 7/1973 | Japan . |
| 0037993 | 3/1982 | Japan .................. 358/88 |
| 61-80221 | 4/1986 | Japan . |

Primary Examiner—John K. Peng
Attorney, Agent, or Firm—Armstrong, Nikaido, Marmelstein, Kubovcik & Murray

[57] ABSTRACT

A stereoscopic electronic endoscope device comprises an electronic endoscope with an image pickup device having a solid-state image sensor located at the tip part of an inserting part and an optical imagery system for creating an image of a shooting object on said solid-state image sensor and enabling observation at two positions where stereoscopic view is possible, an image signal processing device for processing an output signal of said image pickup device, and a stereoscopic image forming device that forms a stereoscopic image of the shooting object using an image signal generated by said image signal processing device based on each output signal of said image pickup device at two positions.

13 Claims, 7 Drawing Sheets

STEREOSCOPIC ELECTRONIC ENDOSCOPE DEVICE

BACKGROUND OF THE INVENTION:

1. Field of the Invention:

The present invention relates to an electronic endoscope device that can observe stereoscopically a shooting object.

2. Related Art Statement:

Recently, various types of electronic endoscope shooting means of solid-state image sensors such as chargecoupled devices (CCD) have been proposed.

Such an electronic endoscope has a resolution higher than that of the fiberscope, facilitating storing or regenerating of images. In addition, there are other advantages such as easy expansion of image and easy processing of comparing to images.

In regard to early detection of cancer, etc., it is often important to identify fine irregularities on a surface. With a conventional electronic endoscope, however, displayed image was so planar that fine ruggedness could not be identified satisfactorily.

Japan Utility Model Application Publication No. 25360/1973 discloses a stereoscopic endoscope using an image guide fiber. With this example known in the prior art, a pair of image guide fibers are required for the right and left eyes, respectively, resulting in a disadvantage that the diameter of the guide fiber becomes large in the entire length of an inserted part.

In addition, Japan Unexamined Patent Publication No. 80221/1986 discloses a technology for stereoscopic vision, in which a stereoscopically visible image is obtained by means of a pair of image inversion prisms and a pair of electronic shutters and then a stereoscopic view is provided by means of a lens which is selectively controlled in synchronization with the electronic shutters. With this example of related technology, however, an optical path to an image sensor element becomes longer, requiring a longer hard tip part of the inserting part of an endoscope, which gives pain to a patient when the inserting part is inserted as a disadvantage of this system.

OBJECT AND SUMMARY OF THE INVENTION

An object of the present invention is to provide a stereoscopic electronic endoscope device which is used to stereoscopically observe a shooting object.

Another object of the present invention is to present a stereoscopic electronic endoscope device which is used for stereoscopic observation without using an inserting part of a large diameter.

Still another object of this invention is to realize a stereoscopic electronic endoscope device available for stereoscopic observation without making the hard tip part of an inserting part unnecessarily long. Still another object of the present invention is to offer a stereoscopic electronic endoscope which is operable for stereoscopic observation using a solid-state image sensor.

The stereoscopic electronic endoscope device based on the present invention comprises a solid-state image sensor and an optical imagery system for forming image on said solid-state image sensor, an electronic endoscope having an image pickup means operable at two positions where a stereoscopic view is made possible, an image signal processing means for processing the output signal of said image pickup means to an image signal, and a stereoscopic image forming means which forms a stereoscopic image of a shooting object using an image signal created by said image signal processing means based on each output signal of said image pickup means at said two positions. Thereby, said shooting object is observed at two positions where stereoscopic view is made possible, in order to form a stereoscopic image of the shooting object.

Other features and advantages of the present invention will be completely understood referring to descriptions given in the following paragraphs.

BRIEF DESCRIPTION OF THE DRAWINGS

FIG. 1 is an explanatory view showing the structure of a stereoscopic electronic endoscope device.

FIG. 2 (A) is a plan view showing the moving mechanism of a solid-state image sensor.

FIG. 2 (B) is a sectional view along a line A-A' of FIG. 2 (A).

FIG. 3 is a side elevation for showing the entire structure of the stereoscopic electronic endoscope device.

FIG. 4 (A) is a timing chart that shows a vertical synchronous signal.

FIG. 4 (B) is a timing chart for a drive pulse applied to the solid-state image sensor.

FIG. 4 (C) is a timing chart for showing a piezoelectric element control pulse.

FIG. 4 (D) is a timing chart which shows the selection of lighting.

FIG. 5 is a block diagram for showing a signal processing circuit for the stereoscopic electronic endoscope device.

FIG. 6 (A) shows a timing chart for a vertical synchronous signal.

FIG. 6 (B) illustrates a timing chart for showing the operation of switch S1.

FIG. 6 (C) is a timing chart that shows the operation of switch S11.

FIG. 6 (D) shows a timing chart related to the operation of switch S21.

FIG. 6 (E) is a timing chart illustrating the operation of switch S12.

FIG. 6 (F) denotes a timing chart for the operation of switch S22.

FIG. 6 (G) is a timing chart that shows the operation of switch S2.

FIG. 6 (H) provides a timing chart for showing the operation switch S13.

FIG. 6 (I) illustrates a timing chart for the operation of switch S23.

FIG. 6 (J) is a timing chart for the operation of switch S14.

FIG. 6 (K) denotes a timing chart for showing the operation of switch S24.

FIG. 6 (L) gives a timing chart for the operation of memory A.

FIG. 6 (M) presents a timing chart showing the operation of memory B.

FIG. 6 (N) relates to a timing chart for the operation of memory C.

FIG. 6 (O) is a timing chart for operation memory D.

FIG. 6 (P) represents a timing chart for showing an image displayed in the monitor.

FIG. 7 is an explanatory view that describes the top part of an electronic endoscope.

FIG. 8 shows the oblique view of an image pickup means.

Referring to FIG. 3, in this electronic endoscope 1, a large diameter operating part 3 is connected to the rear end of an elongated, for example, flexible inserting part 2. From the rear end part of said operating part 3, a flexible cable 4 is extendedly connected towards a side. A connector 5 is equipped at the tip part of this cable 4.

Figure 1:
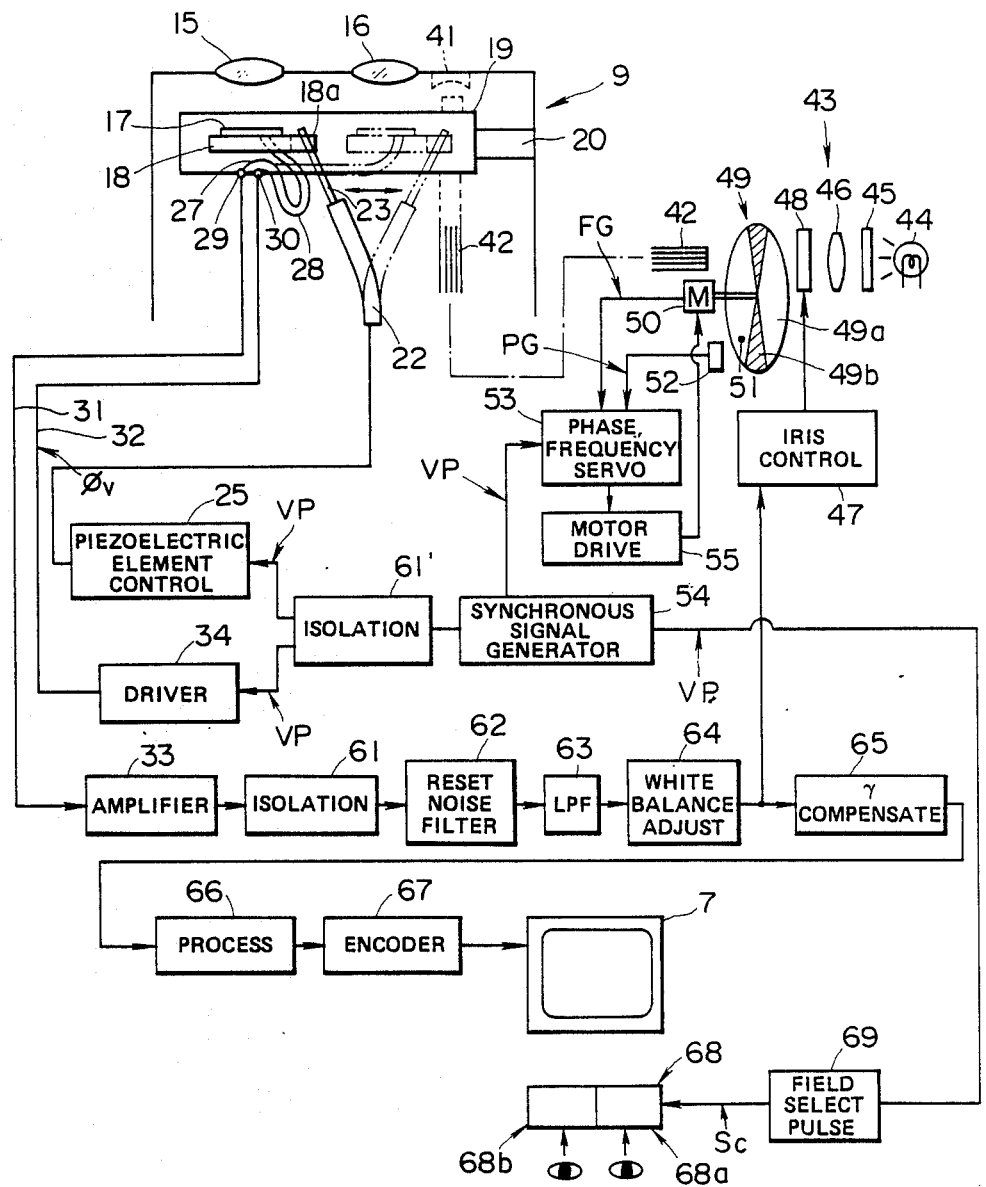
FIGS. 1 through 4 relate to a first embodiment of the present invention.

Said electronic endoscope 1 is to be connected to a control unit 6 which houses a light source unit and an image signal processing circuit. In addition, said control unit 6 is to be connected with a color CRT monitor 7 as a display means.

At the top side of said inserting part 2, there are a hard tip part 9 and a flexible part 10 in the rear side adjacent to said tip part 9, in a sequential manner. A flexing operation knob 11 is equipped in said operating part 3 and operable to rotate in order to flex said flexible part 10 to the left, right, up or down direction.

Referring to FIG. 1, the present embodiment is provided with a pair of object lenses 15, 16 mounted parallel to or inwardly with each other at two positions where a stereoscopic view is made possible at the extremity of said tip part 9. In the imagery position side of said object lenses 15, 16, a solid-state image sensor 17 is provided. In the front face of an image pickup face of said solid-state image sensor 17, a filter array which is not illustrated is fixed, in which color filters of for example red (R), green (G) and blue (B) are arranged in a mosaic manner to transmit these three primary colors.

Figure 2A:
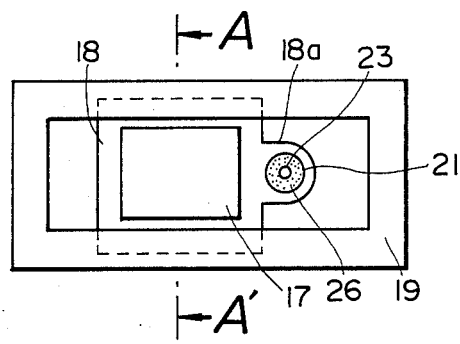
Figure 2B:
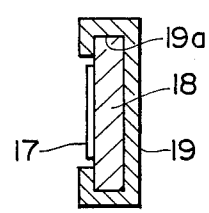
Figure 3:
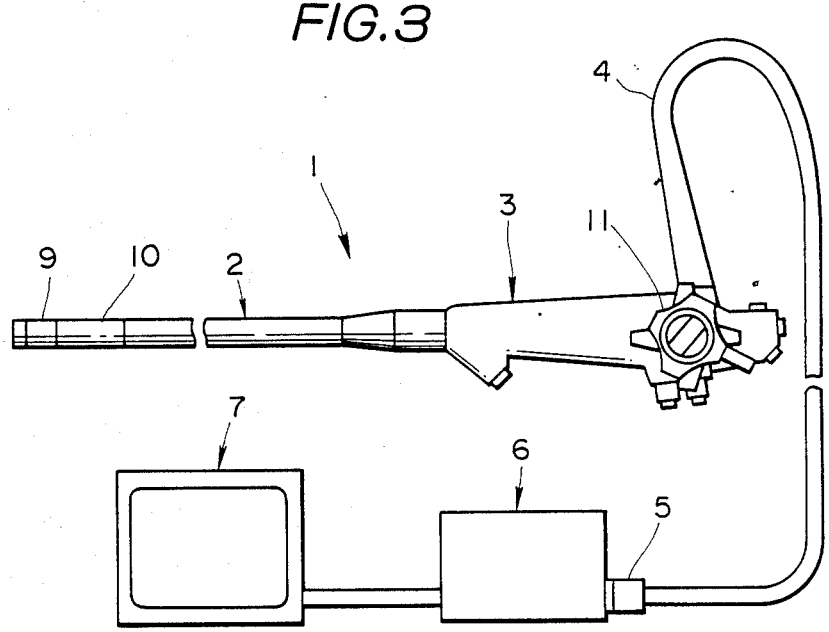

Referring to FIGS. 2 (A) and (B), said solidstate image sensor 17 is fixed on a moving base 18. This moving base 18 is supported by a guide member fixed in the tip part 9, by means of a fixing member 20. Said moving base 18 is said movable in the direction of a straight line connecting said two object lenses 15, 16 along a guide groove 19a of said guide member 19. An extension part 18a is formed at one end side of the moving direction, in which a driving-rod hole 21 is formed in this extension part 18a. In the rear side of said guide member 19, a piezoelectric element 22 of bimorph, etc. is formed in a bar. A driving rod 23 is connected to the top of this piezoelectric element 22. The tip part of the driving rod 23 is inserted in said driving-rod hole 21. Said piezoelectric element 22 is controlled by a piezoelectric element control circuit 25 so that the top end side is deflected and deformed towards the direction of moving said moving base 18. The top side of said driving rod 23 is moved in the direction of moving said moving base 18 according to the deformation of said piezo-electric element 22, thereby said moving base 18 is also driven. In addition, the solid-state image sensor 17 fixed on the moving base 18 is selectably located at an imagery position of any of said two object lenses 15, 16, by moving the moving base 18. Furthermore, a cushion member 26 is equipped in said driving-rod hole 21 for damping any shock when the moving base 18 is driven by said driving rod 23.

Moreover, said solid-state image sensor 17 is connected with a signal line 27 for driving pulses and a signal line 28 for output signals, both having such lengths as to not disturb the movement. These signal lines 27, 28 are connected to connector pins 29, 30 provided on the guide member 19. Connector pins 29, 30 are connected to a preamplifier 33 and a driver 34 provided in said control unit 6 through signal lines 31, 32 inserted in the inserting part 2 and the cable 4, respectively. With such a wiring as above, a weight applied to the piezoelectric element 22 is reduced.

Figure 4:
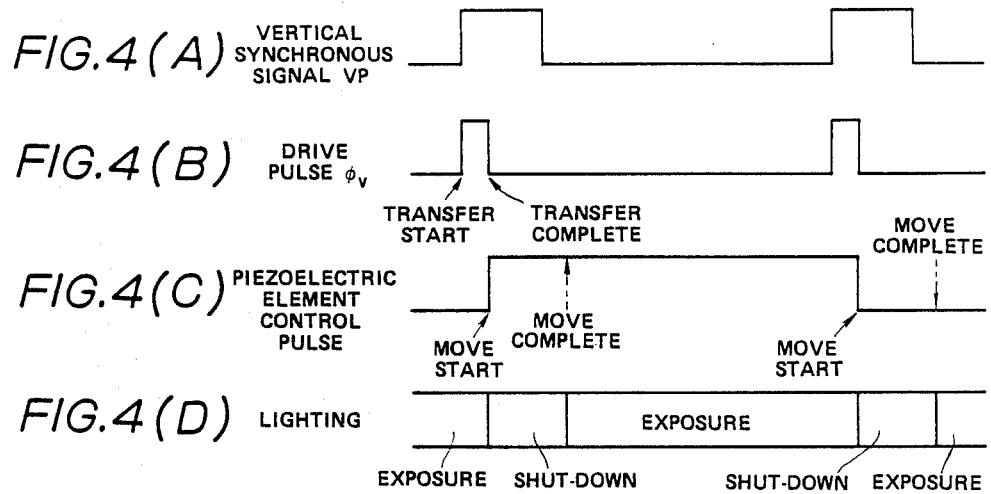

In the top side of said tip part 9, there is a light-distributing lens system 41. In a rear side of the lens system 41, there is a light guide 42 comprising a flexible fiber bundle, connected thereto. The light guide 42 is inserted through said inserting part 2 and cable 4 and connected to a light source unit 43 equipped in said control unit 6. This light source unit 43 is provided with a lamp 44. Light, emitted from the lamp 44, is filter with an infrared cutting filter 45 to filtrate infrared rays, converged with a condenser lens 46, and passes an iris 48 controlled by an iris control circuit 47 and then enters in a rotating filter 49. The rotating filter 49 comprise an exposing unit 49a for transmitting light, dividedly formed in the direction of rotation and a shutter unit 49b for shielding the light and is rotated by a motor 50. The shutter unit 49b is equipped at two positions where the rotating filter 49 revolves one turn per frame period or at one position revolving two turns per frame period. Moreover, a Hall element 51 is attached in the outer periphery of the rotating filter 49. A sensor 52 detects the passage of the Hall element 51 while the phase of its output signal PG is compared with a vertical synchronous signal VP generated from a synchronous signal generator 54 by means of a phase frequency servo circuit 53. In addition, the motor 50 generates a pulse output FG that shows a revolution frequency and is entered in the phase frequency servo circuit 53. The phase frequency servo circuit 53 sends a voltage which represents phase error and speed error, to a motor drive circuit 55 which drives the motor 50. The revolution of the motor 50 is controlled by this voltage. Referring to FIG. 4 (A) and (D), the shutter unit 49b of the rotating filter 49 is synchronized with the vertical synchronous signal VP. Light, transmitted through the rotating filter 49, enters a light guide 42 which leads the light to the tip part 9 and is emitted from the projecting end while irradiating a shooting object through the light-distributing lens system 41.

Light, reflected from the shooting object, passes the object lens system 15 or 16 and is received by the solid-state image sensor 17. The solid-state image sensor 17 accumulates signal charges by means of a photo diode, etc. The signal charges are transferred to a vertical transfer line where an inter line transfer system is used, according to driving pulses $\phi V$ generated from the driver 34. Where the frame transfer system is used, the charges are transferred to the storage unit. Transferred signal charges are sequentially read and sent to the preamplifier 33. Meanwhile, the photo diode stores new charges.

With the present embodiment, the driver 34 receives an input of the vertical synchronous signal VP generated in the synchronous signal generator 54 through isolation treatment device 61'. Referring to FIGS. 4 (A) and (B), the rise of the drive pulse $\phi V$ is synchronized with the rise of the vertical synchronous signal VP.

The vertical synchronous signal VP, after passing through isolation treatment device 61', is also entered in the piezoelectric element control circuit 25. The piezoelectric element control circuit 25 then outputs a piezoelectric element control pulse for deforming the piezoelectric element 22 after the fall time of the drive pulse φV, namely after completion of transferring electric charges stored in the solid-state image sensor 17 as shown in FIG. 4 (C). The piezoelectric element 22 is deformed according to such sensor 17 accumulates signal charges by means of a photo diode, etc. The signal charges are transferred to a vertical transfer line where an inter line transfer system is used, according to driving pulses φV generated from the driver 34. Where the frame transfer system is used, the charges are transferred to the storage unit. Transferred signal charges are sequentially read and sent to the preamplifier 33. Meanwhile, the photo diode stores new charges.

With the present embodiment, the driver 34 receives an input of the vertical synchronous signal VP generated in the synchronous signal generator 54. Referring to FIGS. 4 (A) and (B), the rise of the drive pulse φV is synchronized with the rise of the vertical synchronous signal VP.

The vertical synchronous signal VP is also entered in the piezoelectric element control circuit 25. The piezoelectric element control circuit 25 then outputs a piezoelectric element control pulse for deforming the piezoelectric element 22 after the fall time of the drive pulse φV, namely after completion of transferring electric charges stored in the solid-state image sensor 17 as shown in FIG. 4 (C). The piezoelectric element 22 is deformed according to such a piezoelectric element control pulse. The moving base 18 and the solid-state image sensor 17 are driven according to the deformation of the piezoelectric element 22. The solid-state image sensor 17 is located alternatively at imagery positions of the object lens system 15 and 16 in every other field. Referring to FIGS. 4 (C) and (D), no charges are stored in the solidstate image sensor 17 during a period when the solid-state image sensor 17 is moving, because the shutter unit 49b of the rotating filter 49 is effected to interrupt illuminated light from entering the image guide 42.

According to the principles of the present embodiment, the solid-state image sensor 17 moves during a vertical flyback period while receiving light alternatively through the object lens systems 15 and 16 in every other field. However, light is not received during a moving period.

On the other hand, the output signal from the solid-state image sensor 17 is amplified in the preamplifier 33 and then processed as follows. An isolation treatment 61 applies to insulate a portion which enters in the body of a patient from the signal processing unit, in order to protect the patient from electrical shocks. A reset noise removing treatment 62 is also effected to reduce 1/f noise and reset noise to be generated mainly in the solid-state image sensor 17. Then the output signal is applied to the lowpass filter 63. Furthermore, the white balance of the signal is adjusted in a white balance adjusting circuit. Then a γ compensating circuit 64 compensates the gamma of the signal. The γ compensating circuit 65 is provided to correct non-linear electro-optical conversion characteristics of a CRT with γ=2.2, to linear characteristics in entirety including the electronic endoscope 1. The reciprocal of γ=2.2 namely γ=0.45 is normally used. The output of the γ compensating circuit 65 enters the process circuit 66 by means of which luminance signal and color difference signal are generated. An encoder 67 also generates an image signal from the output of the process circuit 66. The image signal enters a color CRT monitor 7 where the shooting object is displayed in colors.

The output of the white balance adjusting circuit 64 also enters the iris control circuit 47, where the iris 48 is controlled according to the level of a voltage representing an integration of the output signals from the white balance adjusting circuit 64.

The solid-state image sensor 17 receives light transmitted alternatively through the object lens systems 15 and 16 from every other field. Therefore, the monitor 7 alternatively displays, field by field, images with slight offset according to different view fields of the object lens systems 15 and 16.

With the present embodiment, the stereoscopic image of an shooting object is made observable by looking at the image of the monitor 7 through a field select slit 68. The field select slit 68 comprises a right shutter 68a and a left shutter 68b corresponding to the right and left eyes, respectively. Both shutters 68a, 68b are alternatively closed by select pulses Sc generated from a field select pulse generating circuit 69 to which the vertical synchronous signal VP is sent from the synchronous signal generator 54, field by field. The image of the monitor 7 is observed through said field select slit 68, thereby the image of a shooting object is the view field of for example the object lens system 15 observed by the left eye, while using the right eye to watch the image in the view field of the object lens system 16. Accordingly, a stereoscopic image of the shooting object is looked at by the difference of view fields in both object lens systems 15, 16.

In fact, an example of the shutter means is a liquid crystal device in which, when a voltage is not applied, molecules are randomly distributed while shielding of the light takes place, and when the voltage is applied, the molecules are arranged in order transmitting the light.

With the present embodiment structured as described above, the solid-state image sensor 17 moves during vertical flyback period to receive light transmitted alternatively through the object lens systems 15 and 16, field by field while not receiving any light during movement. In other words, the solid-state image sensor 17 shoots the image of a shooting object at two positions where stereoscopic views are given, field after field. The output signal of this solid-state image sensor 17 is processed as an image signal and entered in the monitor 7. This monitor 7 displays two types of images with slight offset according to the difference of view fields in the object lens systems 15, 16 in each field. Images of the monitor 7 are observed by a viewer through the field select slit 68 that shields the left and right eyes alternatively field after field, thus the viewer can observe a stereoscopic image of the shooting object.

With the present embodiment as described above, a viewer can watch a shooting object stereoscopically, thereby any fine ruggedness on the surface of the shooting object is discriminatable facilitating early detection of cancer.

According to this embodiment, the diameter of the inserting part 2 is not made large because a pair of image guides need not be inserted in the unit. When the solid-state image sensor 17 is moving, the solid-state image sensor 17 is not illuminated. Therefore, no ghost occurs.

In addition, only one solid-state image sensor 17 is enough, which can reduce the cost.

Furthermore, the length of the hard tip part 9 is made shorter with this embodiment, which can reduce pain given to a patient when the inserting part 2 is inserted.

Figure 5:
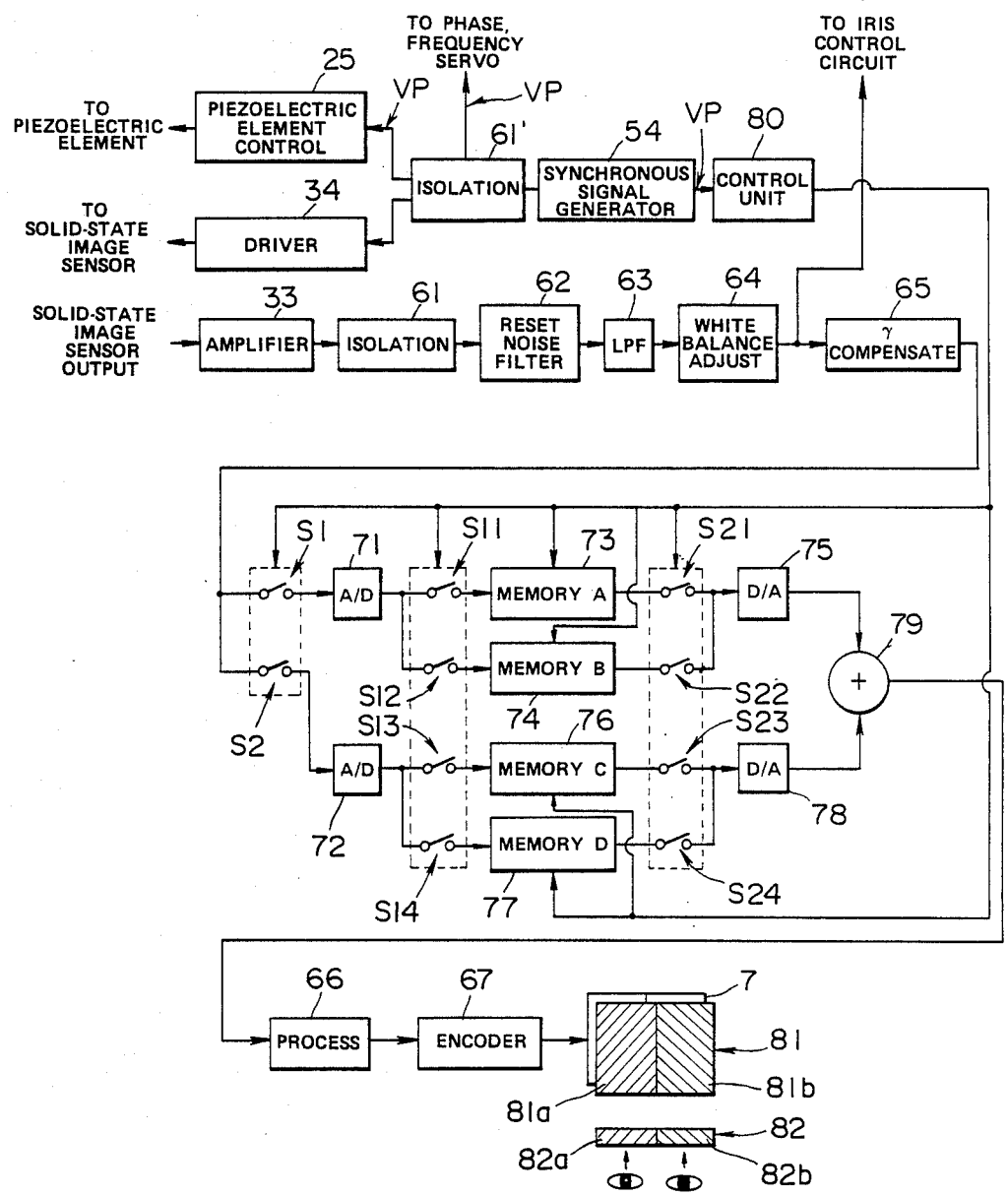
FIGS. 5 and 6 are concerned with a second embodiment of this invention.
Figure 6:
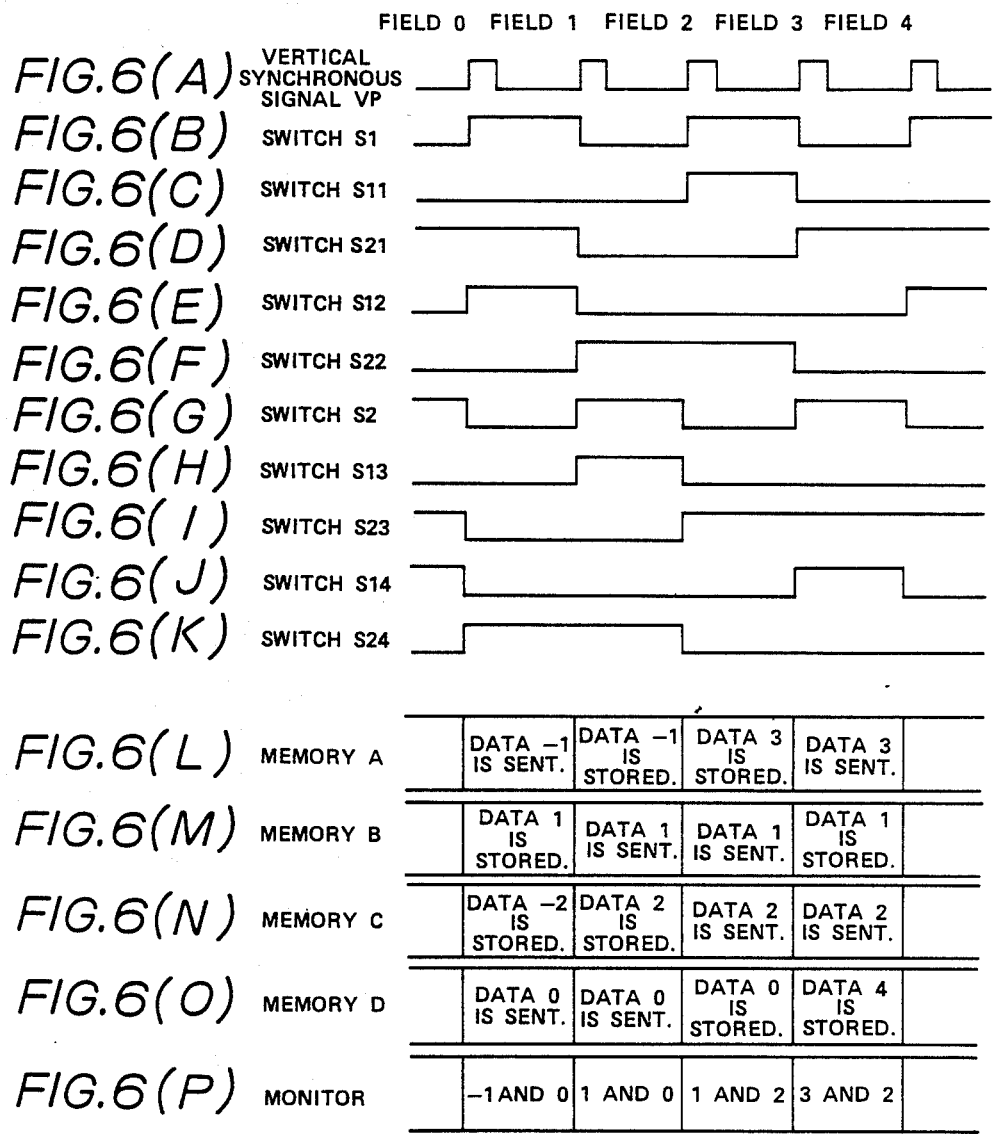

FIGS. 5 and 6 illustrate a second embodiment of the present invention.

With this embodiment, the output signal from the γ compensating circuit 65 is bifurcated and entered into A/D converters 71, 72 through switches S1, S2, respectively, where the signal is converted to digital signals. The output of the A/D converter 71 is further bifurcated and stored in memories A73, B74 via switches S11, S12. Signals, read from memories A73, B74, pass switches S21, S22 respectively and then are converted to analogue signals by a D/A converter 75. The output from the A/D converter 72 is also bifurcated and stored in memories C76, D77 via switches S13, S14, respectively. Signals, read from memories C76, D77, pass through switches S23, S24 respectively and are converted to analogue signals by a D/A converter 78. Outputs of the D/A converters 75, 78 are added in an adder 79.

Now the operation of the switches S1-S24 and the memories A-D73, 74, 76, 77 is described referring to FIGS. 6 (A)-(P). In FIG. 6 (L) through (P), numbers show corresponding field numbers. The switches S1-S24 and memories A-D73, 74, 76, 77 are controlled by a control signal generated in a control unit 80 based on vertical synchronous signal VP sent from the synchronous signal generator 54 shown in FIG. 6 (A). The switches are turned ON and OFF at "H" level and "L" level, respectively.

Referring to FIGS. 6 (B)-(K), there are 4 combinations of switch ON/OFF which are sequentially switched every other field. More explicitly, an example is such that, in field one, switches S1, S21, S12 and S24 are ON while the others are OFF and, in field 2, switches S22, S2, S13 and S24 are ON while the others are OFF and, in field 3, switches S1, S11, S22 and S23 are ON while the others are OFF and, in field 4, switches S21, S2, S23 and S14 are ON while the others are OFF. Subsequently, this sequence is repeated. In odd fields in the above, the solidstate image sensor 17 receives light transmitted through the object lens system 15. In even fields, the solid-state image sensor 17 receives light transmitted through the object lens system 16.

Corresponding to the operation of the switches S1-S24, the memories A-D73, 74, 76, 77 are operated as shown in FIGS. 6 (L)-(O). Referring to memory A shown in FIG. 6 (L) for example, the data stored in field-1 is sent to the D/A converter 75 in field 1. In field 2, the data of field-1 remains still memorized. In field 3, the data of field-3 is stored while, in field 4, the data stored in field-3 is sent to the D/A converter 75. Other memories are operated in a similar manner except in different timings. Consequently, in field 3 for example, the output of the solid-state image sensor 17 receiving light transmitted through the object lens systems 15, in field 3, is stored in memory A73 while converting the data of field 1 stored in memory B74 and the data of field 2 stored in memory C76 to analogue signals by D/A converters 75, 78, respectively. The memory D77 still stores the data of field 0.

Each memory takes such a read timing that one line component of the solid-state image sensor 17 in the analogue signal output generated from the D/A converter 75 is read in the left half of a horizontal period. On the other hand, the analogue signal output generated from the D/A converter 78, corresponding to one line of the solid-state image sensor 17, is read in the right half of a horizontal period according to the read timing of the memory.

Output signals from the D/A converters 75, 78 are added in the adder 79 and then converted to image signals in a process circuit 66 and an encoder 67 while entering the monitor 7. Consequently, as shown in FIG. 6 (P), the monitor 7 displays the image of a shooting object in the object lens system 15 in the odd field, in the left half, while displaying at the same time the image of the shooting object in the view field of the object lens system 16 in the even fields, in the right half.

The present embodiment is equipped with a polarizing plate 81 attached in the front of the monitor 7, which can transmit light in different polarizing directions in the left part 81a and right part 81b. A viewer watches the image of the monitor 7 with polarizing glasses 82 comprising a right part 82a corresponding to the left eye and transmitting only the light in the polarizing direction same as the left side 81a of the polarizing plate 81 and a right part 81b corresponding to the right eye and transmitting only the light in the polarizing direction same as the right part 81b of the polarizing plate 81. Thus, the image of a shooting body in the field of the object lens system 15 is looked at with the left eye while observing the same of the object lens system 16 with the right eye. Accordingly, a stereoscopic image of the shooting object is observable on the basis of different view fields in both object lens systems 15, 16.

The other configurations are the same as the first embodiment.

According to the second embodiment, images of the monitor 7 are watched always with both eyes without flickering.

The other operations and effects are the same as for the first embodiment.

Figure 7:
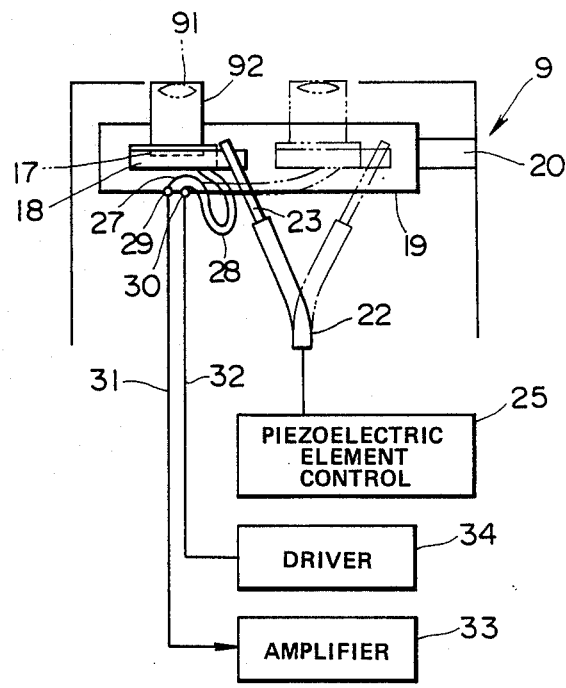
FIG. 7 and 8 are related to a third embodiment of this invention.
Figure 8:
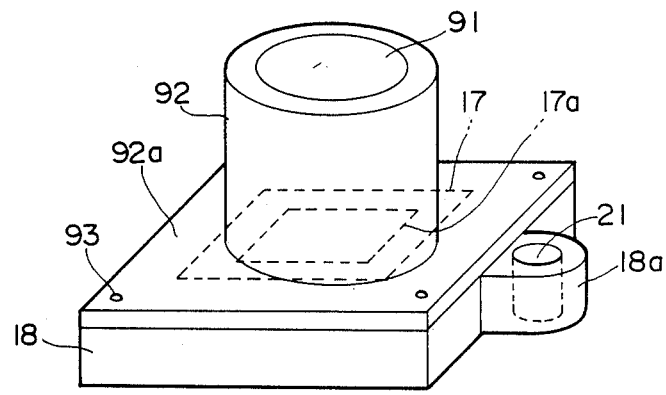

FIGS. 7 and 8 show a third embodiment of this invention.

With this embodiment, the solid-state image sensor 17 is integrated with the object lens system. The solid-state image sensor 17 is fixed on a moving base 18. In the upper part of an image pickup face 17a of the sensor 17, there is an object lens system 91 supported by a cylindrical support frame 92. A bottom part 92a of the support frame 92, formed in a plane, is fixed onto the upper face of the moving base 18 using a screw 93, etc. The object lens system 91 moves in conjunction with the solid-state image sensor 17.

The other configurations, operations and effects are the same as those with the first or second embodiment.

Figure 9:
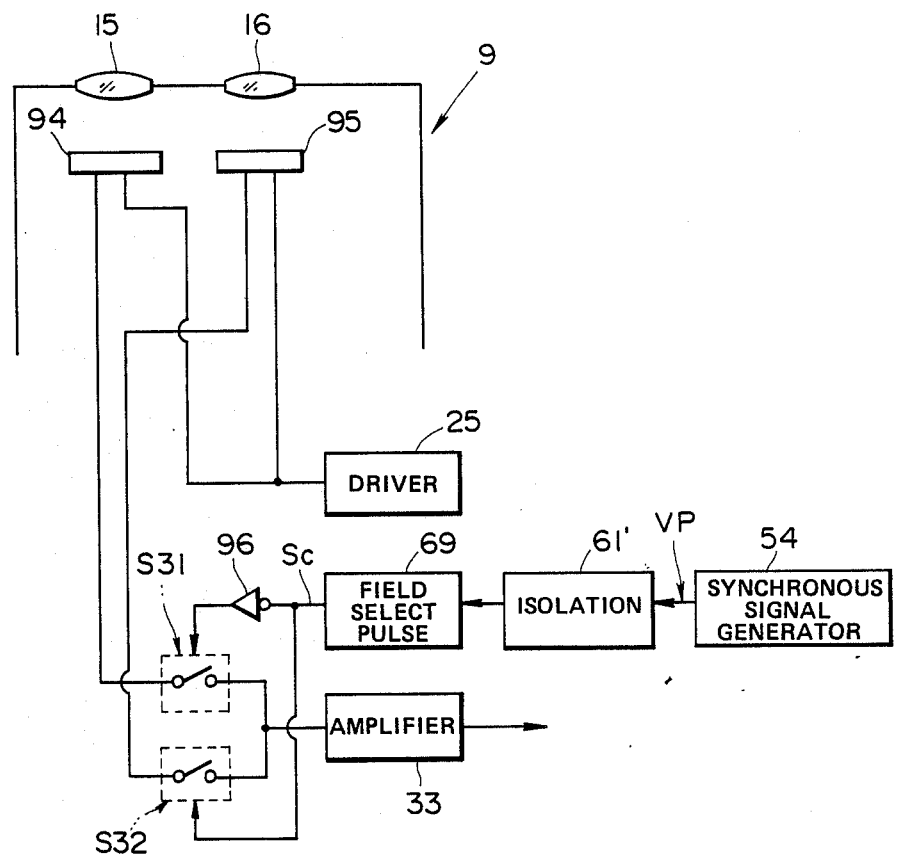
FIG. 9 describes a view of the tip part in an electronic endoscope based on a fourth embodiment of the present invention. Detailed Description of the Preferred Embodiments A first embodiment of the present invention is shown in FIGS. 1 through 4.

FIG. 9 shows a fourth embodiment of the present invention.

In this embodiment, a pair of object lens systems 15, 16 is arranged at two positions where stereoscopic view is made possible, in the top side of the tip part 9. A pair of solid-state image sensors 94, 95 is arranged at imagery positions of the object lens systems 15, 16, respectively. The solid-state image sensors 94, 95 are operated by a driver while their output signals are entered in a preamplifier 33 through switches S31, S32, respectively.

The switches S31, S32 are controlled to turn ON/OFF by select pulses Sc to be output field by field from the field select pulse generating circuit 69 in which the vertical synchronous signal VP is input from the synchronous signal generating circuit 54 through isolation treatment device 61'. The select pulses Sc are applied to switch S31 via an inverter 96 and to switch S32 directly, as opening/closing signals.

The present embodiment is operated, for example, in such a manner that switches S31 and S32 are turned ON and OFF, respectively, in an odd field while sending the output signal of the solid-state image sensor 94 to the preamplifier 33 and, in an even field, switches S31 and S32 are turned OFF and ON, respectively, while sending the output signal of the solid-state image sensor 95 to the preamplifier 33.

Signal processing, in the stages after the preamplifier 33, is the same as the first or second embodiment. However, with the present embodiment, shielding of light during the vertical flyback period is not mandatory.

The other operations and effects are the same as those with the first embodiment.

However, the present invention is not limited only to the foregoing embodiments. For example, a permanent magnet and a coil, etc. may also be used as a means for moving the solid-state image sensor 17.

This invention is applicable not only to a single plate type electronic endoscope where a color filter is mounted in front of the solid-state image sensor but also to a field type electronic endoscope with which illuminating light is sequentially changed from red, to green, blue, etc.

According to the principles of the present invention as described above, an image pickup means comprising a solid-state image sensor and an optical imagery system is made observable at two positions where stereoscopic view is made possible. In addition, a stereoscopic image forming means is provided for forming a stereoscopic image of a shooting object using image signals generated from each output signal at the two positions of the image pickup means. Therefore, an effect that a shooting body is stereoscopically observable using the electronic endoscope is realized.

It is an evident fact that many different embodiments are structured based on the present invention without deviating from the principles and scope of the invention. Therefore, the present invention will not restrict any such embodiments, except for the restrictions by the attached claims.

What is claimed is:

1. A stereoscopic electronic endoscope device comprising:

An electronic endoscope comprising an elongated inserting part and an image pickup means located at a tip part of said inserting part and having a solid-state image sensor and an optical imagery system that works to create an image of a shooting object on said solid-state image sensor, and enabling stereoscopic observation at two positions where stereoscopic view is made possible;

an image signal processing means that processes an output signal from said image pickup means to an image signal; and a stereoscopic image forming means for forming a stereoscopic image of the shooting object using an image signal generated by said image signal processing means based on each output signal at said two positions of the image pickup means.

2. A stereoscopic electronic endoscope device comprising:

an electronic endoscope comprising an elongated inserting part and an image pickup means located at a tip part of said inserting part and having a pair of optical imagery systems arranged at two positions where stereoscopic view is made possible, a solid-state image sensor arrangeable to each imagery position of said pair of optical imagery systems and a moving means that moves said solidstate image sensor to each imagery position of said pair of imagery optical systems;

an image signal processing means that processes an output signal from said solid-state image sensor to an image signal; and a stereoscopic image forming means for forming an stereoscopic image of a shooting object using the image signal generated by said image signal processing means based on each output signal at said both imagery positions of said solid-state image sensor.

3. A stereoscopic electronic endoscope device comprising:

an electronic endoscope comprising an elongated inserting part and an image pickup means located at a tip part of said inserting part and having an optical imagery sensor located at an optical imagery position of said optical imagery system and a moving means that moves said optical imagery system and said solid-state image sensor in an integrated manner alternatively to two positions where stereoscopic view is made possible;

an image signal processing means that processes an output signal of said solid-state image sensor to an image signal; and a stereoscopic image forming means for forming a stereoscopic image of a shooting object using an image signal generated by said image signal processing means based on each output signal at said two positions of said solid-state image sensor.

4. The stereoscopic electronic endoscope device of claim 1, 2 or 3, wherein an illuminating means for illuminating a shooting object is also provided.

5. The stereoscopic electronic endoscope device of claim 2 or 3, wherein said stereoscopic image forming means comprises a monitor that receives an image signal input from said image signal processing means and displays alternatively images picked up at each position by said solid-state image sensor, and a pair of shutters that are shielded alternatively in synchronization with the selecting of images displayed on said monitor, corresponding to left an right eyes.

6. The stereoscopic electronic endoscope device of claim 5, wherein said pair of shutters comprise a liquid crystal device that transmits or shields light depending on whether a voltage is applied or not.

7. The stereoscopic electronic endoscope device of claim 2 or 3, wherein an illuminating means having a means that generates a light shielding period to shield a shooting object from illumination of light in synchronization with the timing of movement by said moving means, is provided.

8. The stereoscopic electronic endoscope device of claim 2 or 3, wherein said moving means moves said solid-state image sensor field by field.

9. The stereoscopic electronic endoscope device of claim 2 or 3, wherein said moving means comprises a piezoelectric configuration.

10. The stereoscopic electronic endoscope device of claim 2 or 3, wherein said stereoscopic image forming means comprises memories that store images picked up by said solid-state image sensor at each position, a monitor that displays an image signal from said image signal processing means, a signal processing means that displays images picked up by said solid-state image sensor at each position respectively in the left and right portions of said monitor, and a restricting means that makes observable alternatively either one of two images displayed in the left and right portions of said monitor.

11. The stereoscopic electronic endoscope device of claim 10, wherein said restricting means is located in front of said monitor and comprises a polarizing plate having a right portion and a left portion that transmit only lights of different polarizing directions, respectively, and polarizing glasses having a right portion corresponding to the right eye and transmitting only the light in the same polarizing direction as the right portion of said polarizing plate and having a left portion corresponding to the left eye and transmitting only the light in the same polarizing directions as the left portion of said polarizing plate.

12. A stereoscopic electronic endoscope device comprising:

an electronic endoscope which comprises an elongated inserting part and an image pickup means located at a tip part of said inserting part and having a pair of optical imagery systems located in at least two positions for stereoscopic viewing, and a pair of solid-state image sensors located at each imagery side of said pair of optical imagery systems;

an image signal processing means for processing an output signal of said image pickup means to an image signal, wherein said image signal processing means comprises a selecting means that alternatively selects either one of output signals from said pair of solid-state image sensors and processes said selected output to an image signal; and a stereoscopic image forming means operably connected to said solid-state image sensors for forming a stereoscopic image of a shooting object using an image signal generated by said image signal processing means based on each output signal of said pair of solid-state image sensors, wherein said stereoscopic image forming means comprises memory that stores images, respectively, picked up by each of said solid-state image sensors, a signal processing means that synthesizes and outputs signals read out of said memories so as to display images picked up by each of said solid-state image sensors on the left and right portions, respectively, of a picture, a monitor that inputs an image signal outputted from said image signal processing means and displays images picked up by each of said solid-state image sensors on the left and right portions, respectively, of said monitor, and a restricting means that makes only one of two different images with each other displayed in the left or right portion of said monitor, corresponding to each of left and right eyes.

13. The stereoscopic electronic endoscope device of claim 12, wherein said restricting means is located in front of said monitor and comprises a polarizing plate having a right portion and a left portion that transmit only the lights of different polarizing directions, respectively, and polarizing glasses having a right portion that correspond to the right eye and transmits only the light of the same polarizing direction as the right portion of said polarizing plate, and having a left portion that corresponds to the left eye and transmits only the light of t the same polarizing direction as the left portion of said polarizing plate.

* * * * *